US012023008B2

(12) United States Patent
Yamaya

(10) Patent No.: US 12,023,008 B2
(45) Date of Patent: Jul. 2, 2024

(54) ENDOSCOPE ATTACHMENT AND ENDOSCOPE SYSTEM

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 549 days.

(21) Appl. No.: 17/236,436

(22) Filed: Apr. 21, 2021

(65) Prior Publication Data

US 2021/0235982 A1     Aug. 5, 2021

Related U.S. Application Data

(63) Continuation of application No. PCT/JP2018/039698, filed on Oct. 25, 2018.

(51) Int. Cl.
*A61B 1/12*  (2006.01)
*A61B 1/00*  (2006.01)

(52) U.S. Cl.
CPC .......... *A61B 1/121* (2013.01); *A61B 1/00087* (2013.01); *A61B 1/00121* (2013.01)

(58) Field of Classification Search
CPC ...... A61B 1/121; A61B 1/00101; A61B 1/122
See application file for complete search history.

(56) References Cited

U.S. PATENT DOCUMENTS

| 3,956,011 | A | * | 5/1976 | Carleton | A61B 1/121 134/22.12 |
| 5,327,881 | A | * | 7/1994 | Greene | A61M 16/0418 600/120 |
| 5,580,530 | A | * | 12/1996 | Kowatsch | A61L 2/14 422/305 |
| 5,746,694 | A | * | 5/1998 | Wilk | A61B 1/121 600/153 |
| 5,840,251 | A | * | 11/1998 | Iwaki | A61B 1/121 422/294 |
| 6,044,855 | A | * | 4/2000 | Monch | A61B 1/125 134/22.12 |

(Continued)

FOREIGN PATENT DOCUMENTS

| EP | 2564757 A1 | 3/2013 |
| JP | S58-172906 U | 11/1983 |

(Continued)

OTHER PUBLICATIONS

International Search Report dated Dec. 25, 2018 issued in PCT/JP2018/039698.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope attachment is an endoscope attachment that is detachably attachable to a distal end portion part of an insertion portion of an endoscope, and includes a cylindrical member that covers a bonding portion that is arranged in a bending portion of the insertion portion and formed of adhesive, and a flow rate varying member that is disposed in the cylindrical member and varies a flow rate of a medicinal solution that enters from an outside of the cylindrical member to an inside of the cylindrical member.

13 Claims, 19 Drawing Sheets

(56) References Cited

U.S. PATENT DOCUMENTS

| | | | |
|---|---|---|---|
| 8,741,069 B2* | 6/2014 | Meyer | A61B 90/70 |
| | | | 134/22.12 |
| 9,931,029 B2* | 4/2018 | Yamaya | A61B 1/123 |
| 10,525,156 B1* | 1/2020 | Bui | A61B 1/121 |
| 11,337,599 B2* | 5/2022 | Yamaya | A61B 1/00098 |
| 2004/0034369 A1* | 2/2004 | Sauer | A61B 1/012 |
| | | | 606/139 |
| 2010/0010310 A1* | 1/2010 | Weisenburgh, II | |
| | | | A61B 1/00091 |
| | | | 600/156 |
| 2012/0289858 A1* | 11/2012 | Ouyang | A61B 1/045 |
| | | | 600/562 |
| 2013/0060083 A1 | 3/2013 | Oku | |
| 2016/0367119 A1* | 12/2016 | Ouyang | A61B 1/0676 |
| 2017/0079520 A1* | 3/2017 | Huang | A61B 1/045 |
| 2017/0150877 A1* | 6/2017 | Yamaya | A61B 1/00128 |
| 2017/0209027 A1* | 7/2017 | Raj | A61B 1/00034 |

FOREIGN PATENT DOCUMENTS

| | | |
|---|---|---|
| JP | H08-196505 A | 8/1996 |
| JP | 2010-005030 A | 1/2010 |
| JP | 2013-052118 A | 3/2013 |
| JP | 2015-181914 A | 10/2015 |
| WO | 2016/059921 A1 | 4/2016 |
| WO | 2017/002932 A1 | 1/2017 |
| WO | 2018/037727 A1 | 3/2018 |

* cited by examiner

ENDOSCOPE ATTACHMENT AND ENDOSCOPE SYSTEM

CROSS REFERENCE TO RELATED APPLICATION

This application is a continuation application of PCT/JP2018/039698 filed on Oct. 25, 2018, the entire contents of which are incorporated herein by this reference.

BACKGROUND OF THE INVENTION

1. Field of the Invention

The present invention relates to an endoscope attachment that is detachably attachable to a distal end portion side of an insertion portion which is used when an endoscope is cleaned or disinfected, and an endoscope system.

2. Description of the Related Art

In recent years, a disease part in a digestive tract system, a pancreas and bile tract system, or the like has been observed and treated using a so-called side-viewing endoscope (hereinafter, simply referred to as an endoscope). In such an endoscope, an observation window, an illumination window, and the like are disposed in a part of an outer circumferential side surface in a distal end portion of an insertion portion inserted into a subject. A configuration is also widely known in which an outer circumferential side surface of a distal end rigid member is covered with a cover in a position except for the observation window, the illumination window, and the like.

In such a side-viewing endoscope, a configuration is also widely known in which a guide wire or treatment instrument is inserted into a pancreatic tract, a bile tract, or a hepatic tract via a channel opening portion using a raising base (forceps elevator) disposed in the distal end portion. The raising base of the endoscope varies a travelling direction of the guide wire or the treatment instrument allowed to be inserted into a channel for allowing insertion of treatment instrument by raising the guide wire or the treatment instrument.

The endoscope needs to be cleaned and disinfected for reuse after use. As described above, a large number of members having irregularities such as the observation window, the illumination window, the raising base, and the channel opening portion described above are disposed on the outer circumferential side surface in the distal end rigid member of the endoscope.

For this reason, to reliably clean and disinfect these irregularities, the cover needs to be removed from the distal end rigid member at the time of clean and disinfection treatment of the members configuring the distal end portion such as the distal end rigid member, the observation window, the illumination window, the raising base, and the channel opening portion, and the members need to be sufficiently cleaned and disinfected by being submerged in a medicinal solution in addition to the normal clean and disinfection treatment of the endoscope.

In such a disinfection procedure of the endoscope, a cleaning tool for an insertion device used together with the endoscope, which is disclosed, for example, in International Publication No. WO2016-059921, is widely known. This conventional cleaning tool is used by being submerged in a medicinal solution in a state in which the cleaning tool is attached to an insertion portion distal end portion. At this time, when a bonding portion formed on a bending portion outer skin is covered with a cylindrical member of the conventional cleaning tool, deterioration of the bonding portion is avoided against the medicinal solution with an intense chemical attack property.

SUMMARY OF THE INVENTION

An endoscope attachment according to an aspect of the present invention is an endoscope attachment that is detachably attachable to a distal end portion part of an insertion portion of an endoscope, and includes a cylindrical member that covers a bonding portion that is arranged in a bending portion of the insertion portion and formed of adhesive, and a flow rate varying member that is disposed in the cylindrical member and varies a flow rate of a medicinal solution that enters from an outside of the cylindrical member to an inside of the cylindrical member.

An endoscope system according to an aspect of the present invention includes an endoscope, and an endoscope attachment that is detachably attachable to a distal end portion part of an insertion portion of an endoscope, the endoscope attachment including a cylindrical member that covers a bonding portion that is arranged in a bending portion of the insertion portion and formed of adhesive, and a flow rate varying member that is disposed in the cylindrical member and varies a flow rate of a medicinal solution that enters from an outside of the cylindrical member to an inside of the cylindrical member.

DETAILED DESCRIPTION OF THE PREFERRED EMBODIMENTS

Hereinafter, embodiments of the present invention will be described with reference to the drawings. Note that the drawings are schematic drawings and it should be emphasized that a relationship between a thickness and a width of each of members, ratios of the thicknesses of the respective members, and the like are different from actual dimensions, and, of course, parts having different mutual dimensional relationships and ratios are also included between the mutual drawings.

Figure 1:
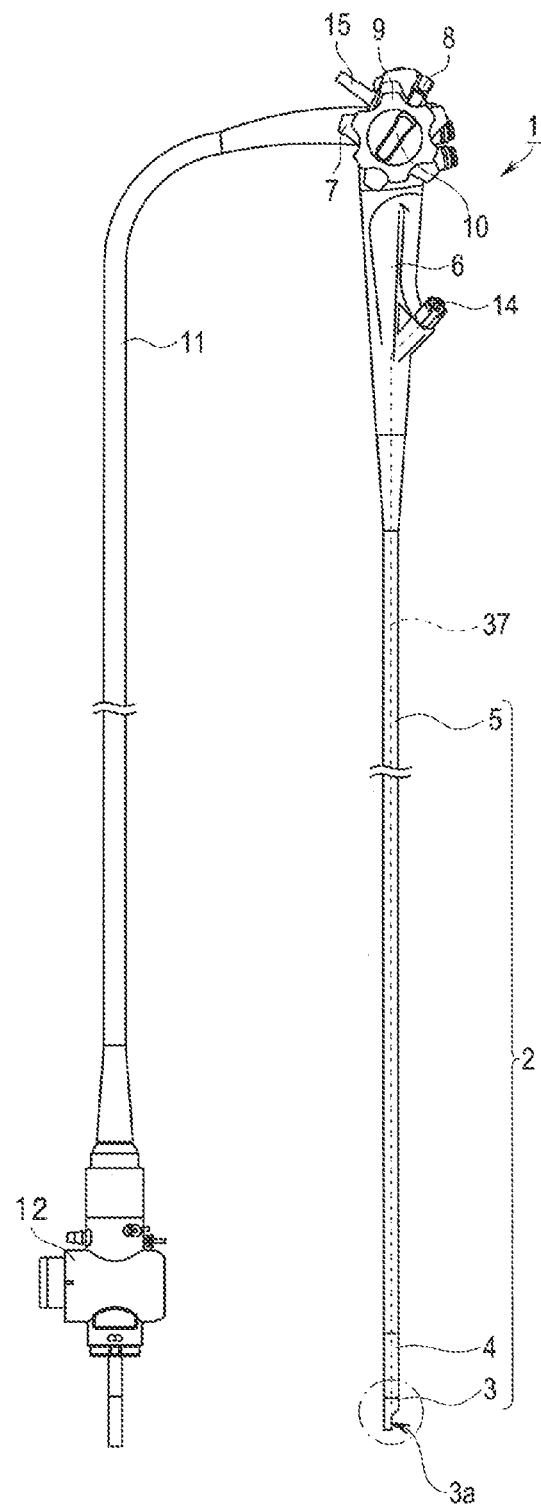
FIG. 1 is a diagram illustrating a configuration of an endoscope in a state in which a distal end cover is detached where a distal end portion side of an insertion portion is cleaned and disinfected by an endoscope attachment according to the present embodiment.
Figure 2:
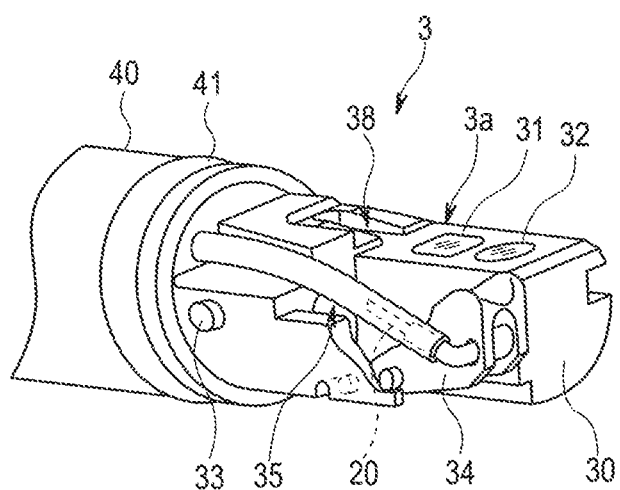
FIG. 2 is a perspective view illustrating a configuration of a distal end portion in a state in which the distal end cover is detached according to the present embodiment.

FIG. 1 is a diagram illustrating a configuration of an endoscope in a state in which a distal end cover is detached where a distal end portion side of an insertion portion is cleaned and disinfected by an endoscope attachment according to the present embodiment, and FIG. 2 is a perspective view illustrating a configuration of a distal end portion in a state in which the distal end cover is detached.

As illustrated in FIG. 1, an endoscope 1 of an endoscope system includes an insertion portion 2 inserted into a subject, an operation portion 6 continuously disposed on a proximal end side in an insertion direction of the insertion portion 2, a universal cord 11 extending from the operation portion 6, and a connector 12 disposed at an extension end of the universal cord 11 to configure a main portion. Note that the endoscope 1 is electrically connected to an external apparatus such as a control apparatus or an illumination apparatus via the connector 12.

The insertion portion 2 is configured by including a distal end portion 3, a bending portion 4, and a flexible tube portion 5 in the stated order from a distal end side, and is formed to be elongated towards the distal end side in the insertion direction.

An up and down bending operation knob 7 that bends the bending portion 4 in an up and down direction, and a left and right bending operation knob 9 that bends the bending portion 4 in a left and right direction are disposed in the operation portion 6.

A fixing lever 8 that fixes a turning position of the up and down bending operation knob 7, and a fixing knob 10 that fixes a turning position of the left and right bending operation knob 9 are also disposed in the operation portion 6.

The bending portion 4 is continuously disposed on the proximal end side of the distal end portion 3. The bending portion 4 is bent in four directions including up, down, left, and right by turning operations of the up and down bending operation knob 7 and the left and right bending operation knob 9, for example. According to this, an observation direction of an observation window 31 disposed in the distal end portion 3 which will be described below is varied, and also an insertion property of the distal end portion 3 in the subject is improved.

A raising base operation knob 15 that is turned and operated when a raising base (forceps elevator) 34 disposed in the distal end portion 3 which will be described below is raised or lowered is further disposed in the operation portion 6.

A treatment instrument insertion opening 14 for allowing insertion of a guide wire or treatment instrument which is not illustrated in the drawing into a channel 37 for allowing insertion of treatment instrument which serves as a tubular passage disposed in the insertion portion 2 of the endoscope 1 is also disposed in the operation portion 6.

As illustrated in FIG. 2, a distal end rigid member 30 that configures a frame and is also formed of metal, for example, is disposed in the distal end portion 3. A recessed notched portion 3a where one outer circumferential surface side of the distal end rigid member 30 is notched is also formed on an outer circumferential surface of the distal end portion 3. An air/water feeding channel opening portion 38 serving as an opening of the distal end portion 3 of an air/water feeding channel is formed on one outer circumferential surface of the notched portion 3a.

The observation window 31 and an illumination window 32 are also disposed on one outer circumferential surface of the notched portion 3a in the vicinity of the air/water feeding channel opening portion 38. Note that a distal end cover which will be described below is disposed to cover a circumference of the distal end rigid member 30 except for the raising base 34, a channel opening portion 35, the observation window 31, and the illumination window 32.

The raising base 34 is further disposed at a position facing the channel opening portion 35 in the distal end rigid member 30. The raising base 34 varies a travelling direction of the treatment instrument or the guide wire allowed to be inserted from the treatment instrument insertion opening 14 into the channel 37 for allowing insertion of treatment instrument in a raising and falling manner. According to this, the raising base 34 leads the treatment instrument or the guide wire to a desired position in the subject along with raising.

The raising base 34 can rise and fall due to pulling or relaxation of a wire 20 allowed to be inserted into the insertion portion 2 and the operation portion 6 by the turning operation of the raising base operation knob 15.

Note that the bending portion 4 is connected to the distal end rigid member 30 on the proximal end side. The bending portion 4 is covered with an outer skin 40 that is bending rubber configured of rubber or the like which configures an outer circumferential surface. A thread wound bonding portion 41 serving as a distal end side bonding portion is formed on the outer skin 40 after a distal end part is wound around an outer circumference of the distal end rigid member 30 by a thread and fixed and attached by, for example, epoxy-based adhesive.

A thread wound bonding portion 42 serving as a proximal end side bonding portion is also formed on the outer skin 40 after a proximal end part is wound around a distal end outer circumference of the flexible tube portion 5 by a thread and fixed and attached by the adhesive similarly as in the thread wound bonding portion 41.

Next, a distal end attachment 50 serving as an endoscope attachment of the present embodiment will be described in detail.

Figure 3:
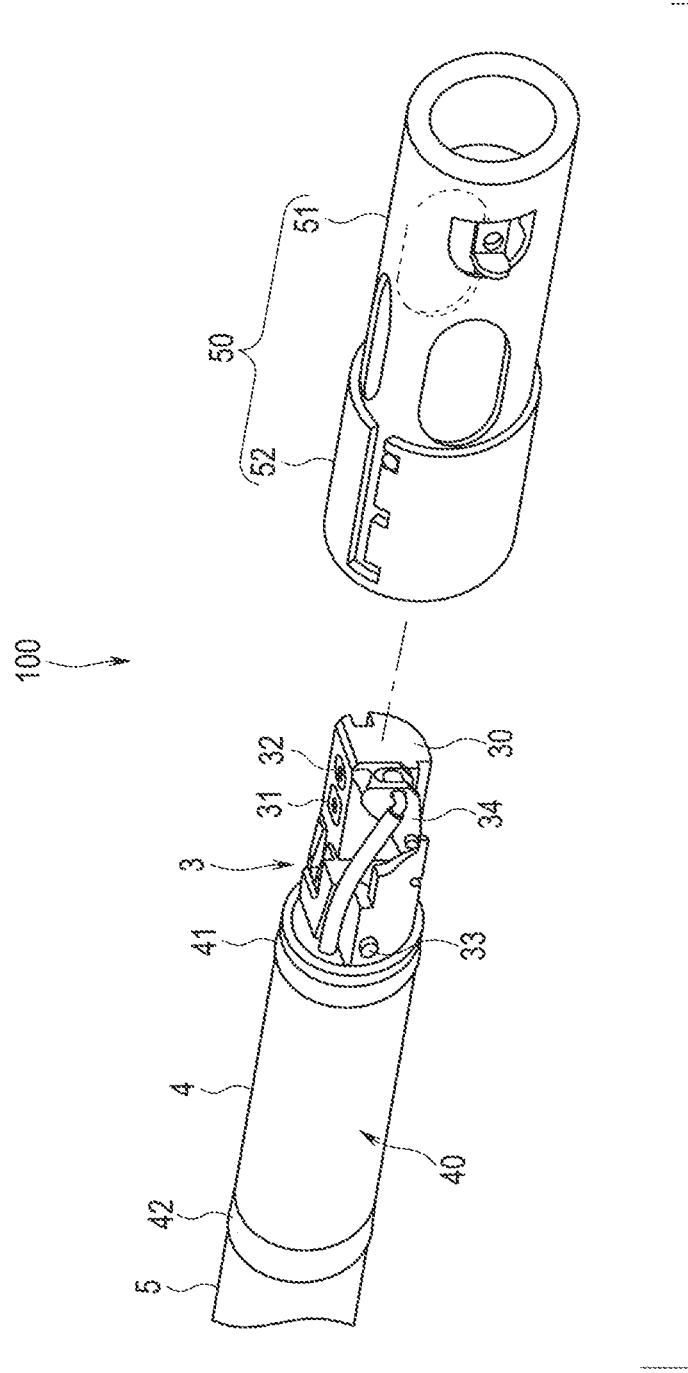
FIG. 3 is a perspective view illustrating a configuration of the distal end portion of the endoscope and a distal end attachment according to the present embodiment.
Figure 4:
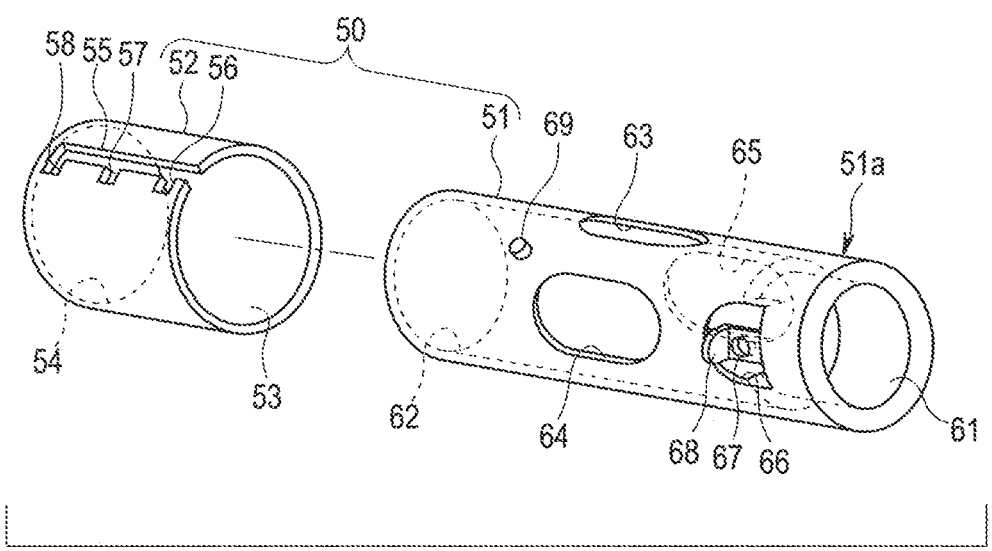
FIG. 4 is an exploded perspective view illustrating a configuration of the distal end attachment according to the present embodiment.

FIG. 3 is a perspective view illustrating a configuration of the distal end portion of the endoscope and the distal end attachment, and FIG. 4 is an exploded perspective view illustrating a configuration of the distal end attachment.

As illustrated in FIG. 3, in the distal end attachment 50 included in the endoscope system, a flow rate varying mechanism portion is configured which varies a flow rate of a fluid that enters from an outside to an inside by two cylindrical bodies including a main body cylinder 51 that is a cylindrical member serving as a long inner tube and a slide cylinder 52 that is a flow rate varying member serving as a short external tube disposed in the main body cylinder 51. Note that the distal end attachment 50 and the endoscope 1 configure an endoscope system 100 according to the present embodiment.

As illustrated in FIG. 4, the main body cylinder 51 of the distal end attachment 50 has the opening portions 61 and 62 in the front and the back, and includes a distal end rigid member holding portion 51a in which an inner diameter of the distal end side is formed to be gradually smaller in stages, which is a resin material like polysulfone or a flexible resin tube such as silicone. Note that the main body cylinder 51 may be formed of a rigid metal such as stainless steel.

In the main body cylinder 51, a plurality of, three herein, oval opening windows 63, 64, and 65 serving as window portions are disposed in a middle part along a longitudinal axis (hole axis of the cylindrical body). The three opening windows 63, 64, and 65 include a same length along the longitudinal axis of the main body cylinder 51, and are formed at a same position with a predetermined interval about an outer circumference of the main body cylinder 51.

Note that the number of the opening windows 63, 64, and 65 is not limited to three, and may be one, or may also be multiple like two or more. A hole portion 66 is also formed in a part of the outer circumference of the distal end part of the main body cylinder 51, and an engagement releasing lever 68 in which an engagement hole 67 is disposed is integrally formed with the hole portion 66.

In the main body cylinder 51, a locking pin 69 serving as a slide pin that protrudes from an outer circumferential surface of the proximal end part on a rear side of the opening windows 63, 64, and 65 is disposed. The locking pin 69 may be integrally formed with the main body cylinder 51, or may also be a separate body from the main body cylinder 51 and attached to an outer circumferential portion by bonding, screwing, or the like.

The slide cylinder 52 of the distal end attachment 50 has opening portions 53 and 54 in the front and the back, and is a resin material like polysulfone or a flexible resin tube such as silicone similarly as in the main body cylinder 51. Note that the slide cylinder 52 may also be formed of a rigid metal such as stainless steel.

The slide cylinder 52 has a slide groove 55 formed on the proximal end side along a longitudinal axis (hole axis of the cylindrical body) from the opening portion 53 at the distal end. The slide groove 55 has a plurality of, three herein, pin locking portions 56, 57, and 58 serving as locking grooves having a predetermined interval in a circumferential direction of the slide cylinder 52.

In other words, in the slide groove 55, the pin locking portion 56 serving as a first locking groove, the pin locking portion 57 serving as a second locking groove, and the pin locking portion 58 serving as a third locking groove are formed in an outer circumferential direction of the slide cylinder 52 to have a predetermined length in the stated order from the distal end side in a direction substantially orthogonal to a linear groove in a longitudinal direction of the slide cylinder 52.

The slide cylinder 52 is externally inserted from the proximal end side of the main body cylinder 51, and the locking pin 69 protruding from the outer circumferential surface of the main body cylinder 51 is locked into the slide groove 55. At this time, when the slide cylinder 52 turns about the longitudinal axis, the locking pin 69 of the main body cylinder 51 is locked into any of the pin locking portions 56, 57, and 58 of the slide groove 55 and is locked so as not to move in a longitudinal direction of the main body cylinder 51.

The distal end attachment 50 of the present embodiment configured as described above can vary opening amounts of the three opening windows 63, 64, and 65 of the main body cylinder 51 in three stages herein in accordance with a locking position of the locking pin 69 of the main body cylinder 51 at the pin locking portions 56, 57, and 58 of the slide groove 55 formed in the slide cylinder 52.

In other words, in accordance with the slide cylinder 52, a coverage area of the distal end part of the insertion portion 2 in the distal end attachment 50 can be varied.

Figure 5:
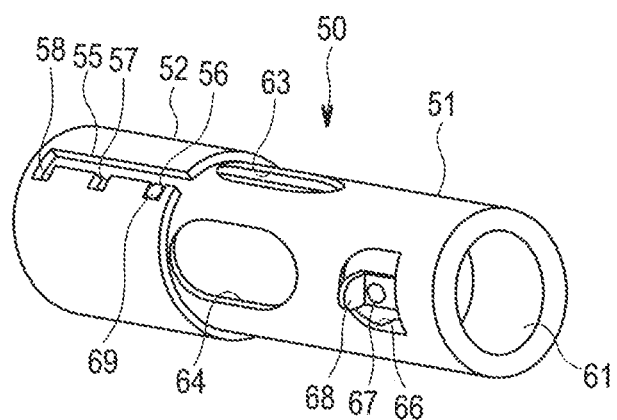
FIG. 5 is a perspective view illustrating a configuration of a distal end attachment in a first state in which a locking pin is locked into a first locking groove according to the present embodiment.
Figure 6:
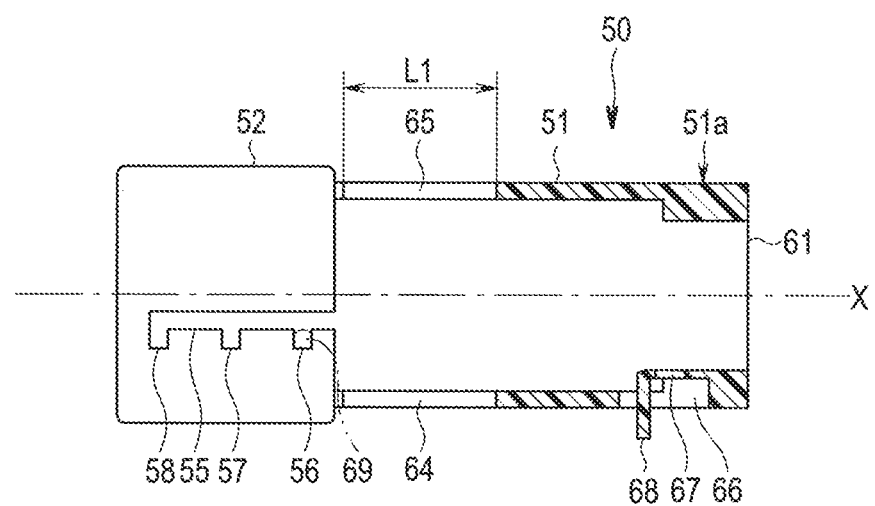
FIG. 6 is a partial cross-sectional view illustrating a configuration of the distal end attachment in the first state in which the locking pin is locked into the first locking groove according to the present embodiment.

FIG. 5 is a perspective view illustrating a configuration of a distal end attachment in a first state in which a locking pin is locked into a first locking groove, and FIG. 6 is a partial cross-sectional view illustrating a configuration of the distal end attachment in the first state in which the locking pin is locked into the first locking groove.

First, as illustrated in FIG. 5 and FIG. 6, in a state in which the locking pin 69 of the main body cylinder 51 is locked into the pin locking portion 56 serving as the first locking groove of the slide groove 55 formed in the slide cylinder 52, the distal end attachment 50 is put into a state in which an entirety of the three opening windows 63, 64, and 65 of the main body cylinder 51 is exposed. In other words, the slide cylinder 52 is locked at a position where the three opening windows 63, 64, and 65 of the main body cylinder 51 are not covered.

Note that the three opening windows 63, 64, and 65 have a predetermined length L1 along a longitudinal axis X, and are put into a state in which a range at the predetermined length L1 is all exposed without being covered. According to this, the entirety of the three opening windows 63, 64, and 65 of the main body cylinder 51 is put into an exposed state.

At this time, the distal end attachment 50 is put into the first state in which the opening amounts (opening areas) of the three opening windows 63, 64, and 65 are maximized.

Figure 7:
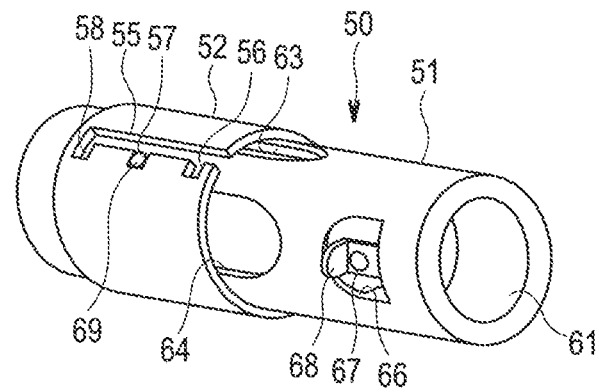
FIG. 7 is a perspective view illustrating a configuration of the distal end attachment in a second state in which the locking pin is locked into a second locking groove according to the present embodiment.
Figure 8:
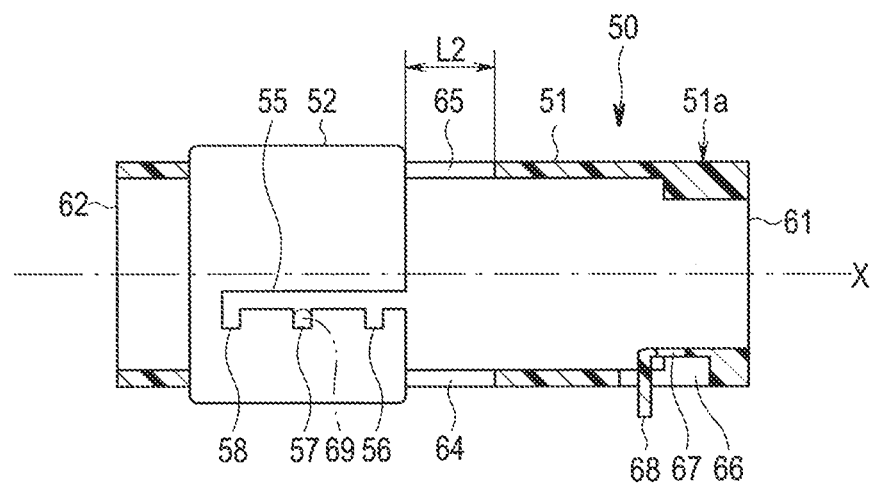
FIG. 8 is a partial cross-sectional view illustrating a configuration of the distal end attachment in the second state in which the locking pin is locked into the second locking groove according to the present embodiment.

FIG. 7 is a perspective view illustrating a configuration of the distal end attachment in a second state in which the locking pin is locked into a second locking groove, and FIG. 8 is a partial cross-sectional view illustrating a configuration of the distal end attachment in the second state in which the locking pin is locked into the second locking groove.

Next, as illustrated in FIG. 7 and FIG. 8, in a state in which the locking pin 69 of the main body cylinder 51 is locked into the pin locking portion 57 serving as the second locking groove of the slide groove 55 formed in the slide cylinder 52, the distal end attachment 50 is put into a state in which a part of the three opening windows 63, 64, and 65 of the main body cylinder 51, for example, approximately a half is exposed. In other words, the slide cylinder 52 is locked at a position where a part of the three opening windows 63, 64, and 65 of the main body cylinder 51, for example, approximately a half is covered.

In this state, the three opening windows 63, 64, and 65 are put into an exposed state in which only a range at a predetermined length L2 (L1>L2) shorter than the predetermined length L1 in the first state along the longitudinal axis X is not covered. According to this, a part of the three opening windows 63, 64, and 65 of the main body cylinder 51, for example, approximately a half (½), is put into an exposed state.

At this time, the distal end attachment 50 is put into the second state in which the opening amounts (opening areas) of the three opening windows 63, 64, and 65 are smaller than the opening amounts in the first state.

Figure 9:
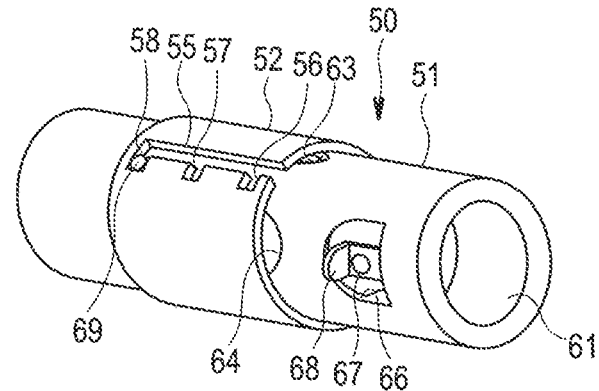
FIG. 9 is a perspective view illustrating a configuration of the distal end attachment in a third state in which the locking pin is locked into a third locking groove according to the present embodiment.
Figure 10:
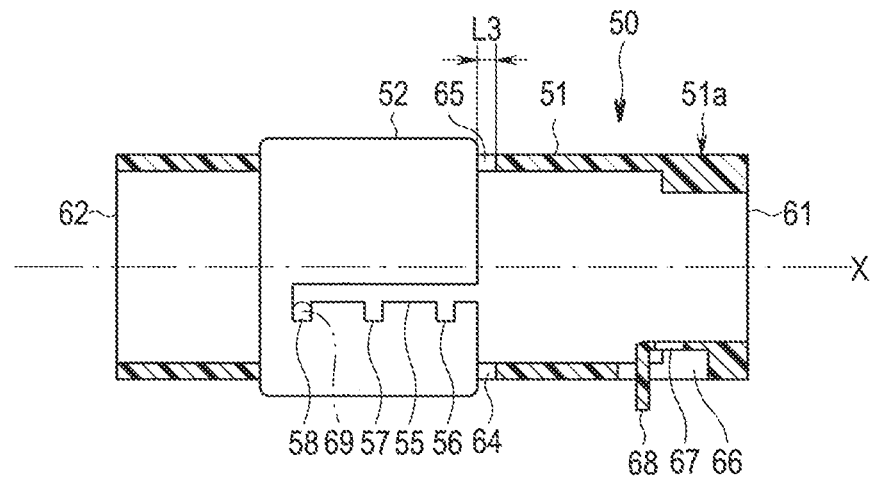
FIG. 10 is a partial cross-sectional view illustrating a configuration of the distal end attachment in the third state in which the locking pin is locked into the third locking groove according to the present embodiment.

FIG. 9 is a perspective view illustrating a configuration of the distal end attachment in a third state in which the locking pin is locked into a third locking groove, and FIG. 10 is a partial cross-sectional view illustrating a configuration of the distal end attachment in the third state in which the locking pin is locked into the third locking groove.

Next, as illustrated in FIG. 9 and FIG. 10, in a state in which the locking pin 69 of the main body cylinder 51 is locked into the pin locking portion 58 serving as the third locking groove of the slide groove 55 formed in the slide cylinder 52, the distal end attachment 50 is put into a state in which the three opening windows 63, 64, and 65 of the main body cylinder 51 are exposed slightly, for example, by approximately ⅕ to 1/10 relative to the entirety. In other words, the slide cylinder 52 is locked at a position where a majority, for example, approximately ⅘ to 9/10, of the three opening windows 63, 64, and 65 of the main body cylinder 51 is covered.

In this state, the three opening windows 63, 64, and 65 are put into a state in which a range at a predetermined length (L1>L2>L3) still shorter than the predetermined length L1 in the first state and the predetermined length L2 in the second state along the longitudinal axis X is exposed without being covered. According to this, the three opening windows 63, 64, and 65 of the main body cylinder 51 are put into a slightly exposed state, for example, by approximately ⅕ to 1/10 relative to the entirety.

At this time, the distal end attachment 50 is put into the third state in which the opening amounts (opening areas) of the three opening windows 63, 64, and 65 are still smaller than the opening amounts (opening areas) in the second state.

Note that the opening amounts (opening areas) of the three opening windows 63, 64, and 65 in the first state, the second state, and the third state described above are one example, and can be appropriately changed in accordance with formation positions of the pin locking portions 56, 57, and 58 of the slide groove 55.

Here, a procedure for cleaning and disinfecting the endoscope 1 by using the distal end attachment 50 of the present embodiment will be described below.

Figure 11:
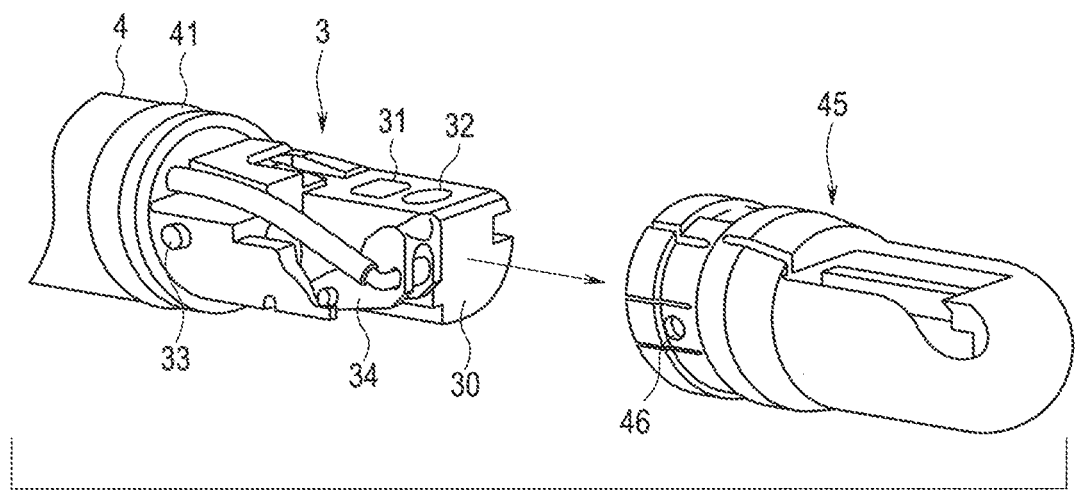
FIG. 11 is a perspective view illustrating a state in which the distal end cover is detached from a distal end rigid member according to the present embodiment.
Figure 12:
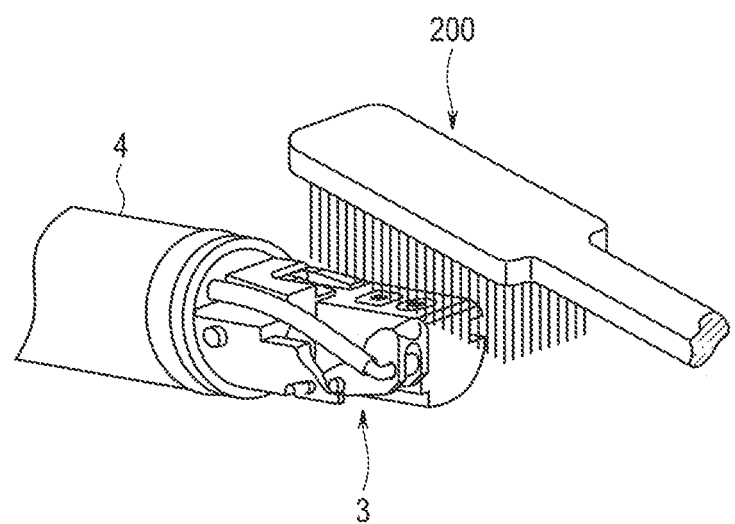
FIG. 12 is a perspective view illustrating a state in which the distal end rigid member is brushed by a cleaning brush according to the present embodiment.

FIG. 11 is a perspective view illustrating a state in which the distal end cover is detached from the distal end rigid member, and FIG. 12 is a perspective view illustrating a state in which the distal end rigid member is brushed by a cleaning brush.

As illustrated in FIG. 11, the distal end cover 45 is detached from the distal end rigid member 30 of the endoscope 1. Note that the distal end rigid member 30 includes an engagement pin 33 that is engaged with an engagement hole 46 formed in the distal end cover 45 and fixes the attachment of the distal end cover 45.

As illustrated in FIG. 12, brushing cleaning is performed on the distal end rigid member 30 by a cleaning brush 200 under running water. After this brushing cleaning, the distal end attachment 50 is externally inserted and attached onto the distal end part of the insertion portion 2 in an axis direction of the distal end rigid member 30.

Next, a state will be described below in which the distal end attachment 50 is attached to the distal end part of the insertion portion 2, and the endoscope 1 is submerged and disinfected in a medicinal solution. Note that the medicinal solution herein refers to a liquid having a chemical attack property such as cleaning or disinfection.

Figure 13:
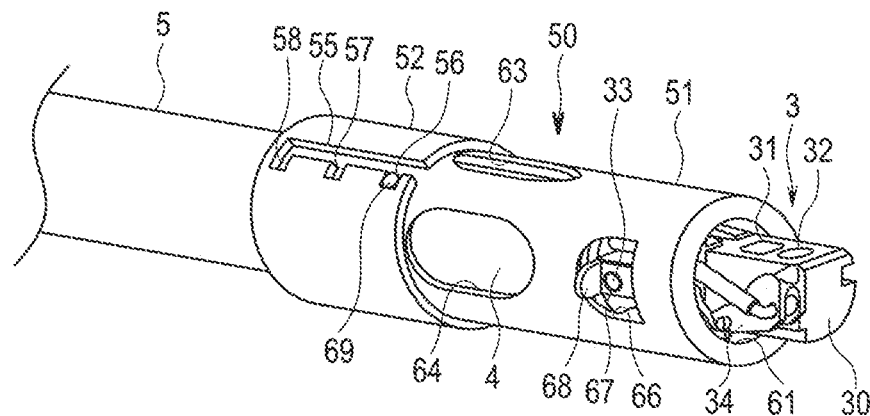
FIG. 13 is a perspective view illustrating a state in which the distal end attachment in the first state is attached to the distal end part of the insertion portion according to the present embodiment.
Figure 14:
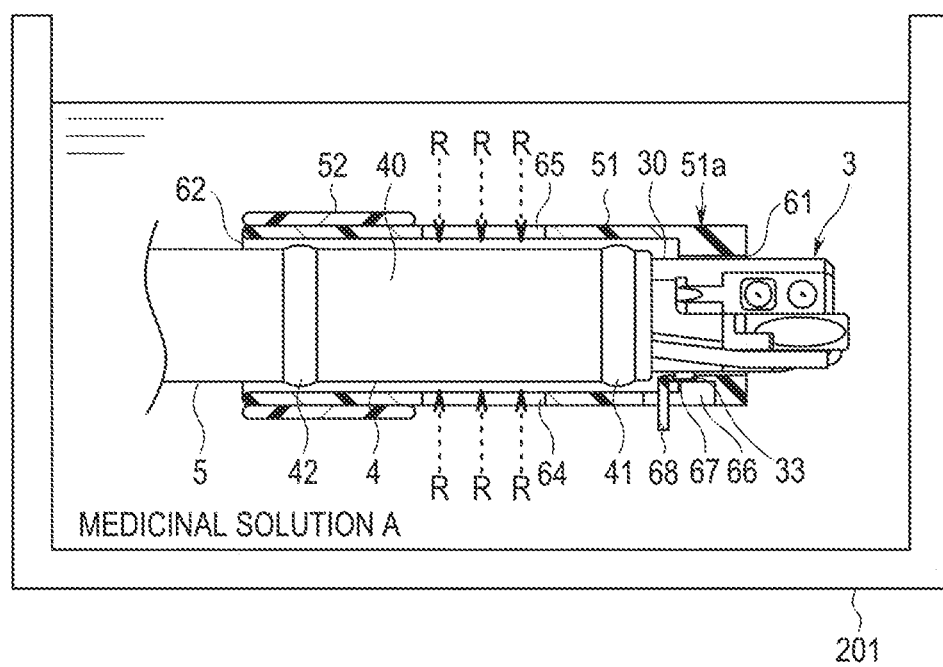
FIG. 14 is a partial cross-sectional view illustrating a distal end part of the insertion portion to which the distal end attachment in the first state is attached, and illustrating a state in which the distal end part is submerged in a medicinal solution with a weak chemical attack property according to the present embodiment.
Figure 15:
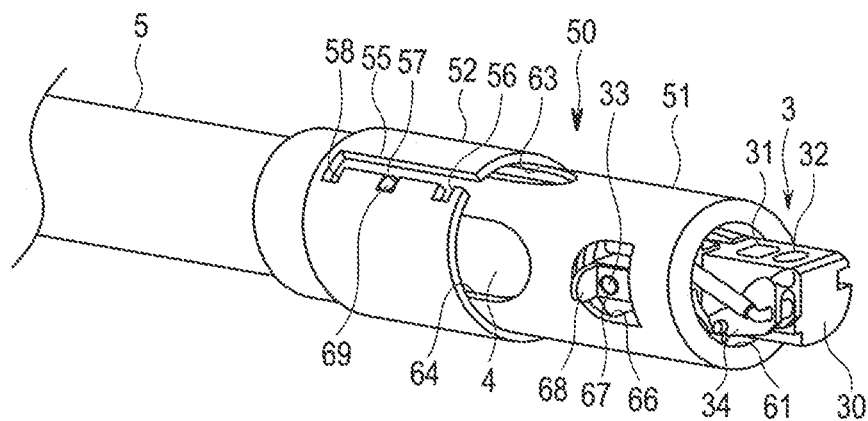
FIG. 15 is a perspective view illustrating a state in which the distal end attachment in the second state is attached to the distal end part of the insertion portion according to the present embodiment.
Figure 16:
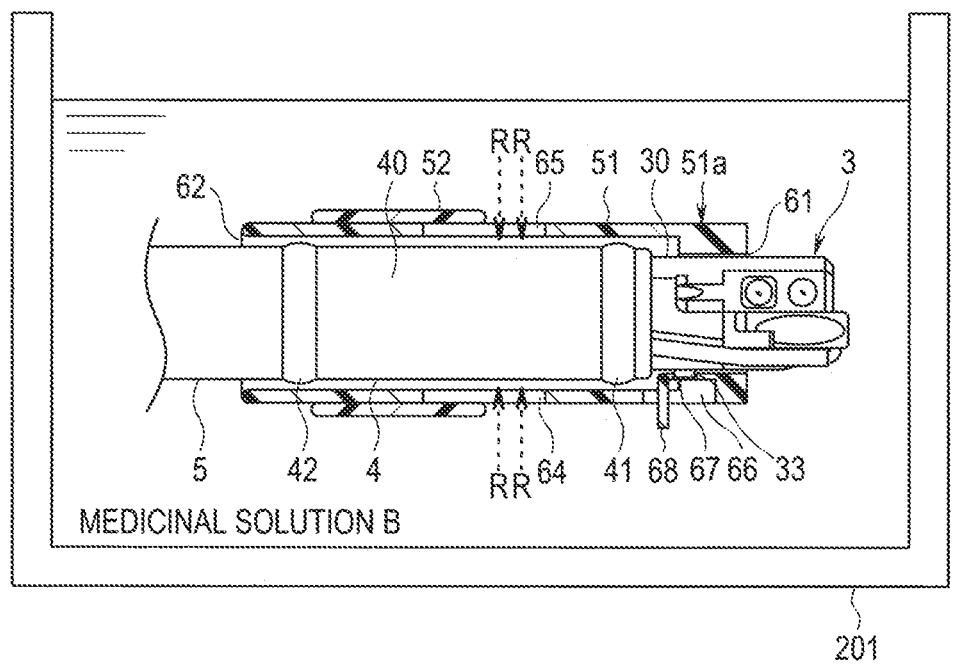
FIG. 16 is a partial cross-sectional view illustrating the distal end part of the insertion portion to which the distal end attachment in the second state is attached, and illustrating a state in which the distal end part is submerged in a medicinal solution with an intermediate chemical attack property according to the present embodiment.
Figure 17:
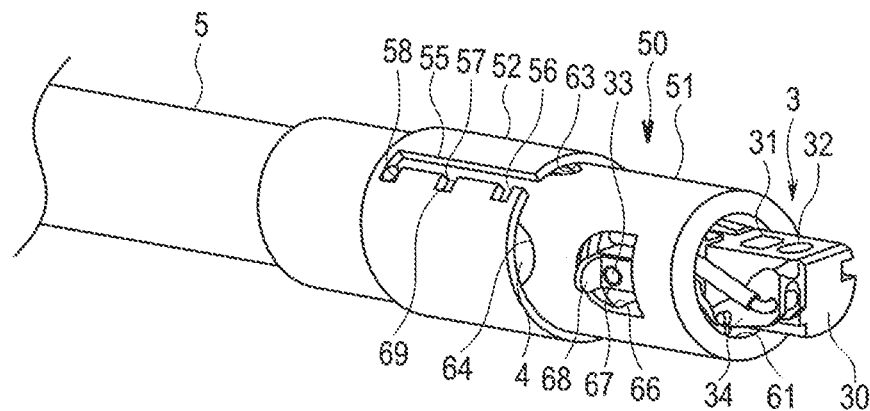
FIG. 17 is a perspective view illustrating a state in which the distal end attachment in the third state is attached to the distal end part of the insertion portion according to the present embodiment.
Figure 18:
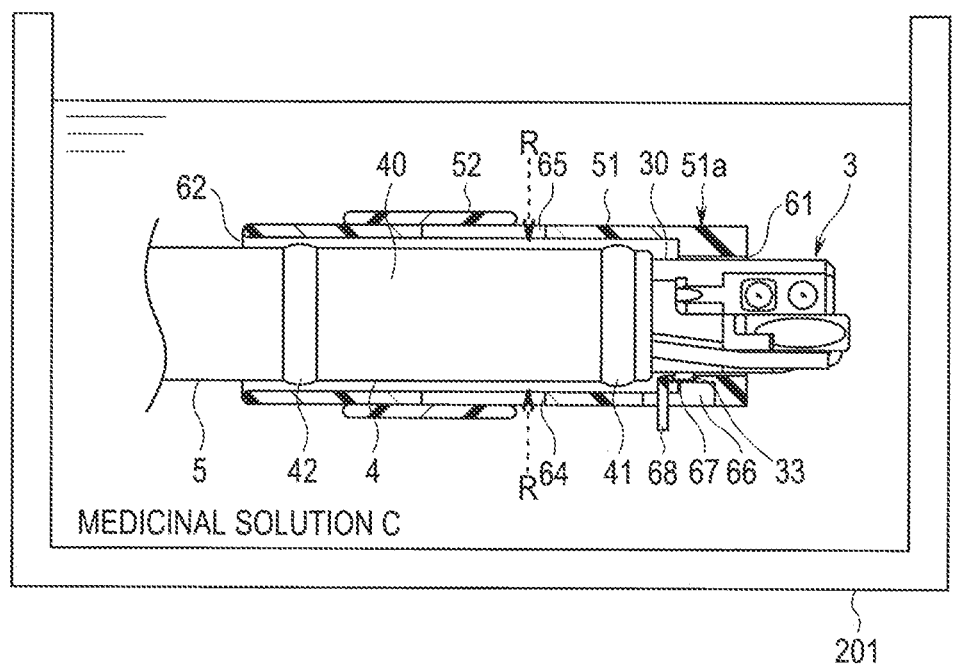
FIG. 18 is a partial cross-sectional view illustrating the distal end part of the insertion portion to which the distal end attachment in the third state is attached, and illustrating a state in which the distal end part is submerged in a medicinal solution with an intense chemical attack property according to the present embodiment.

FIG. 13 is a perspective view illustrating a state in which the distal end attachment in the first state is attached to the distal end portion of the insertion portion, FIG. 14 is a partial cross-sectional view illustrating a distal end part of the insertion portion to which the distal end attachment in the first state is attached, and illustrating a state in which the distal end part is submerged in a medicinal solution with a weak chemical attack property, FIG. 15 is a perspective view illustrating a state in which the distal end attachment in the second state is attached to the distal end portion of the insertion portion, FIG. 16 is a partial cross-sectional view illustrating the distal end part of the insertion portion to which the distal end attachment in the second state is attached, and illustrating a state in which the distal end part is submerged in a medicinal solution with an intermediate chemical attack property, FIG. 17 is a perspective view illustrating a state in which the distal end attachment in the third state is attached to the distal end portion of the insertion portion, and FIG. 18 is a partial cross-sectional view illustrating the distal end part of the insertion portion to which the distal end attachment in the third state is attached, and illustrating a state in which the distal end part is submerged in a medicinal solution with an intense chemical attack property.

As illustrated in FIG. 13, the distal end attachment 50 is attached to the distal end part of the insertion portion 2 with a predetermined gap that communicates with the outside. Note that herein, the distal end attachment 50 represents the first state in which the opening amounts (opening areas) of the three opening windows 63, 64, and 65 are maximized.

At this time, the distal end rigid member 30 protrudes from the opening portion 61 on the distal end side of the main body cylinder 51 of the distal end attachment 50, and as illustrated in FIG. 14, is held with a predetermined gap in the distal end rigid member holding portion 51a disposed in the distal end part of the main body cylinder 51.

When the distal end attachment 50 is attached to the distal end rigid member 30, the engagement pin 33 of the distal end rigid member 30 is engaged with the engagement hole 67 formed in the engagement releasing lever 68 and attached and fixed. In other words, in the distal end rigid member 30, the engagement pin 33 is shared to attach and fix the distal end cover 45 and the distal end attachment 50.

Note that when the distal end attachment 50 is detached from the distal end rigid member 30, the engagement between the engagement pin 33 and the engagement hole 67 can be released by tilting the engagement releasing lever 68 towards the distal end side.

In this manner, the distal end part of the insertion portion 2 of the endoscope 1 in which the distal end attachment 50 is attached to the distal end rigid member 30 is in a state in which the thread wound bonding portion 41 serving as the distal end side bonding portion and the thread wound bonding portion 42 serving as the proximal end side bonding portion which are disposed in the front and the back of the bending portion 4 of the insertion portion 2 are covered with the main body cylinder 51.

In other words, the main body cylinder 51 of the distal end attachment 50 has a length in a longitudinal axis X direction with which the thread wound bonding portions 41 and 42 disposed in the front and the back of the bending portion 4 can be covered.

Note that the three opening windows 63, 64, and 65 are located between the thread wound bonding portions 41 and 42 so that the thread wound bonding portions 41 and 42 disposed in both ends of the bending portion 4 of the insertion portion 2 arranged in the distal end attachment 50 are not exposed.

In other words, when the opening windows 63, 64, and 65 are located between the front and back thread wound bonding portions 41 and 42, the chemical attack property can be adjusted for the thread wound bonding portions 41 and 42 at a comparable level.

The endoscope 1 to which the distal end attachment 50 is attached is submerged and disinfected in a container body 201 such as a sink, a cleaning tank, or a disinfection tank that stores a medicinal solution such as a cleaning solution or an antiseptic solution.

In this manner, in a state in which the distal end attachment 50 is attached to the distal end part of the insertion portion 2, when the endoscope 1 is submerged in the medicinal solution, the thread wound bonding portions 41 and 42 arranged in the front and the back of the bending portion 4 covered with the distal end attachment 50 do not contact the container body 201.

For this reason, the thread wound bonding portions 41 and 42 are protected by the distal end attachment 50, and avoid being scratched by being in contact with the container body 201 or the like. Even in a case where the endoscope 1 is submerged in the medicinal solution for a constant period of time, it is possible to decrease a deterioration rate caused by the chemical attack property due to the medicinal solution to the thread wound bonding portions 41 and 42 covered with the distal end attachment 50.

After the opening amounts (opening areas) of the three opening windows 63, 64, and 65 are adjusted in accordance with the chemical attack property depending on a type of the medicinal solution, the distal end attachment 50 of the present embodiment is attached to the distal end rigid member 30.

To describe in detail, for example, in the case of a medicinal solution A with a low cleaning disinfection property and a weak chemical attack property (glutaral-based antiseptic solution or the like), as illustrated in FIG. 13 and FIG. 14, the distal end attachment 50 is attached to the distal end rigid member 30 by adjusting a position of the slide cylinder 52 relative to the main body cylinder 51 to be put into the first state in which the opening amounts (opening areas) of the three opening windows 63, 64, and 65 are maximized.

In this state, convection of the medicinal solution A that enters from the three opening windows 63, 64, and 65 to the distal end part side of the insertion portion 2 easily occurs, and a flow rate R including a convection speed, a convection amount, or the like into the distal end attachment 50 can be increased. According to this, a decrease in the cleaning disinfection property of the distal end part of the insertion portion 2 due to the medicinal solution A with the weak cleaning disinfection property can be prevented.

Note that since the chemical attack property of the medicinal solution A is weak, even when the flow rate R for the convection to the thread wound bonding portions 41 and 42 covered with the distal end attachment 50 is increased, an influence on the deterioration is small.

For example, in the case of a medicinal solution B with a more intense cleaning disinfection property than the cleaning disinfection property of the medicinal solution A and an intermediate chemical attack property (medicinal solution that is more intense than the glutaral-based antiseptic solution or the like and weaker than a peracetic-based antiseptic solution or the like), as illustrated in FIG. 15 and FIG. 16, the distal end attachment 50 is attached to the distal end rigid member 30 by adjusting the position of the slide cylinder 52 relative to the main body cylinder 51 to be put into the second state in which the opening amounts (opening areas) of the three opening windows 63, 64, and 65 are substantially halved.

In this state, the convection of the medicinal solution B that enters from the three opening windows 63, 64, and 65 to the distal end part side of the insertion portion 2 is less likely to occur as compared with the convection of the medicinal solution A described above, and the flow rate R into the distal end attachment 50 can also be decreased. Note that even in accordance with the medicinal solution B with the intermediate cleaning disinfection property, it is possible to sufficiently clean and disinfect the distal end part of the insertion portion 2.

Note that since the medicinal solution B has the intermediate chemical attack property that is more intense than the chemical attack property of the medicinal solution A, the flow rate R for the convection to the thread wound bonding portions 41 and 42 covered with the distal end attachment 50 is set to be lower than the flow rate R of the medicinal solution A, and it is possible to suppress the deterioration rate of the thread wound bonding portions 41 and 42.

For example, in the case of a medicinal solution C with an intense cleaning disinfection property and an intense chemical attack property (peracetic-based antiseptic solution or the like), as illustrated in FIG. 17 and FIG. 18, the distal end attachment 50 is attached to the distal end rigid member 30 by adjusting the position of the slide cylinder 52 relative to the main body cylinder 51 to be put into the third state in which the opening amounts (opening areas) of the three opening windows 63, 64, and 65 are small.

In this state, the convection of the medicinal solution C that enters from the three opening windows 63, 64, and 65 hardly occurs to the distal end part side of the insertion portion 2, and it is possible to decrease the flow rate R into the distal end attachment 50. In this manner, the flow rate R for the convection to the thread wound bonding portions 41 and 42 covered with the distal end attachment 50 is decreased, and it is possible to suppress the deterioration rate of the thread wound bonding portions 41 and 42.

Note that herein, in accordance with the medicinal solution C with the intense cleaning disinfection property, it is possible to sufficiently perform the cleaning and disinfection even when the flow rate to the distal end part side of the insertion portion 2 is low.

As described above, the distal end attachment 50 of the present embodiment can change the position of the slide cylinder 52 relative to the main body cylinder 51 in accordance with intensity and weakness of the cleaning disinfection property and the chemical attack property of the medicinal solutions A, B, and C to be used, and vary the opening amounts of the three opening windows 63, 64, and 65 in the three stages herein.

According to this, the distal end attachment 50 is used when the endoscope is cleaned and disinfected, and can have a configuration in which for the chemical attack property in accordance with a cleaning disinfection performance depending on a type of the medicinal solutions A, B, and C, the thread wound bonding portions 41 and 42 disposed at both ends of the bending portion 4 of the insertion portion 2 are covered to suppress the deterioration rate, and the sufficient cleaning disinfection property can be ensured.

(First Modification)

Figure 19:
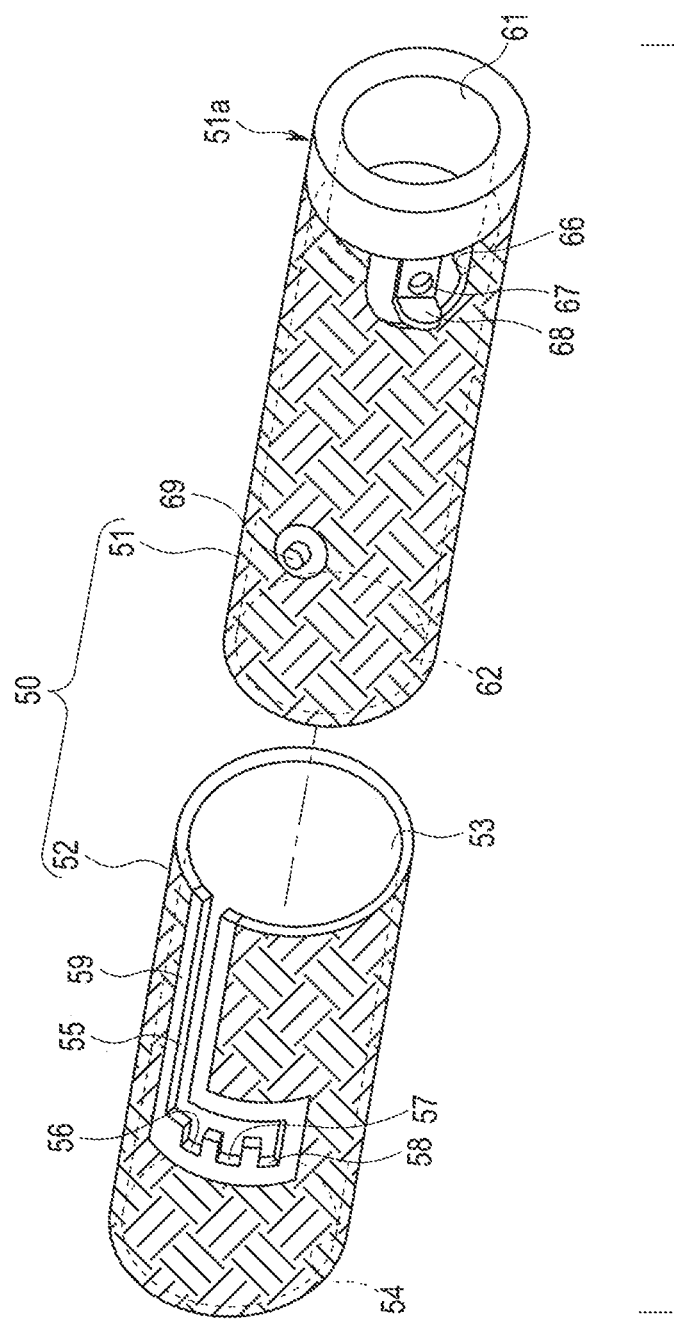
FIG. 19 is an exploded perspective view illustrating a configuration of the distal end attachment of a first modification.
Figure 20:
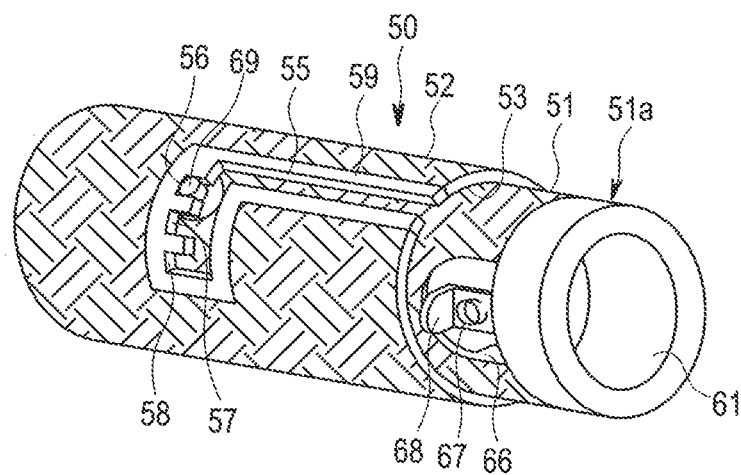
FIG. 20 is a perspective view illustrating a configuration of the distal end attachment in the first state in which the locking pin is locked into the first locking groove according to the first modification.
Figure 21:
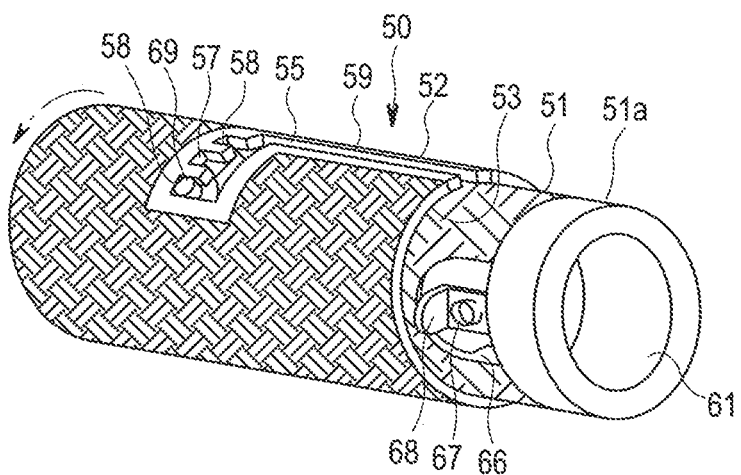
FIG. 21 is a perspective view illustrating a configuration of the distal end attachment in the third state in which the locking pin is locked into the third locking groove according to the first modification.

FIG. 19 is an exploded perspective view illustrating a configuration of the distal end attachment of a first modification, FIG. 20 is a perspective view illustrating a configuration of the distal end attachment in the first state in which the locking pin is locked into the first locking groove according to the first modification, and FIG. 21 is a perspective view illustrating a configuration of the distal end attachment in the third state in which the locking pin is locked into the third locking groove according to the first modification.

As illustrated in FIG. 19, in the distal end attachment 50 serving as endoscope auxiliary instrument of the present modification, the main body cylinder 51 and the slide cylinder 52 are like steel tubes that are meshed cylindrical bodies.

The main body cylinder 51 includes the distal end rigid member holding portion 51a in which the distal end part is formed of a resin material such as polysulfone or silicone or a metal such as stainless steel, and the meshed cylindrical body is connected to the distal end rigid member holding portion 51a.

Note that in the main body cylinder 51, the engagement releasing lever 68 is integrally formed with the distal end rigid member holding portion 51a, and the locking pin 69 is disposed in an outer circumferential portion of the main body cylinder 51 similarly as in the embodiment described above.

The slide cylinder 52 has an L-shaped member 59 formed of a resin material such as polysulfone or silicone or a metal such as stainless steel in which the slide groove 55 is formed, and is a meshed cylindrical body a part of which is configured by the L-shaped member 59.

The slide groove 55 herein is formed to be linear along the longitudinal axis of the slide cylinder 52, and is a substantially L-shaped groove in which a proximal end is disposed to extend so as to be substantially orthogonal to the circumferential direction of the slide cylinder 52. A groove part disposed to extend in the circumferential direction of the slide cylinder 52 has a plurality of, three herein, pin locking portions 56, 57, and 58 serving as locking grooves having a predetermined interval in a proximal end direction.

Note that the slide cylinder 52 has a length at which the proximal end side of the main body cylinder 51 is covered from the vicinity of the engagement releasing lever 68, and is externally inserted onto the main body cylinder 51.

The slide cylinder 52 is turned about the longitudinal axis and slid towards the front, and the locking pin 69 of the main body cylinder 51 is locked into any of the pin locking portions 56, 57, and 58 of the slide groove 55 to realize the locking so that the movement about the longitudinal axis of the main body cylinder 51 does not occur.

More specifically, as illustrated in FIG. 20, in a state in which the locking pin 69 of the main body cylinder 51 is locked into the pin locking portion 56 serving as the first locking groove of the slide groove 55 formed in the slide cylinder 52, the distal end attachment 50 is put into a state in which respective reticulations of the main body cylinder 51 and the slide cylinder 52 are matched and overlapped with each other.

At this time, the distal end attachment 50 is put into the first state corresponding to a course state in which the reticulations of the mesh-like main body cylinder 51 and the mesh-like slide cylinder 52 are matched with each other, and are therefore not blocked up with each other.

As illustrated in FIG. 21, in a state in which the locking pin 69 of the main body cylinder 51 is locked into the pin locking portion 58 serving as the third locking groove of the slide groove 55 formed in the slide cylinder 52, the distal end attachment 50 is put into a state in which the reticulations of the main body cylinder 51 and the slide cylinder 52 are in a shifted state by not being matched with each other.

At this time, the distal end attachment 50 is put into the third state corresponding to a dense state in which the respective reticulations of the mesh-like main body cylinder 51 and the mesh-like slide cylinder 52 are not matched with each other, and are therefore blocked up with each other by a predetermined amount.

Note that although not illustrated in the drawing, in a state in which the locking pin 69 of the main body cylinder 51 is locked into the pin locking portion 57 serving as the second locking groove of the slide groove 55 formed in the slide cylinder 52, the distal end attachment 50 is put into a state in which the reticulations of the main body cylinder 51 and the slide cylinder 52 are slightly shifted from each other.

Since the respective reticulations of the mesh-like main body cylinder 51 and the mesh-like slide cylinder 52 are slightly shifted from each other, the distal end attachment 50 is put into the second state corresponding to a state between the first state and the third state.

In this manner, the distal end attachment 50 can set the mesh-like main body cylinder 51 and the mesh-like slide cylinder 52 to be meshed, and can vary the state from coarse to dense in three stages herein in accordance with the turning position about the longitudinal axis of the slide cylinder 52.

Even with such a configuration, the distal end attachment 50 can change the flow rate of the medicinal solution that enters the inside in accordance with the intensity and weakness of the cleaning disinfection property and the chemical attack property.

Note that the main body cylinder 51 and the slide cylinder 52 are meshed, but a configuration may also be adopted where a plurality of hole portions and the like are formed in the main body cylinder 51 and the slide cylinder 52, and an overlapping state of the plurality of hole portions in accordance with the turning position about the longitudinal axis of the slide cylinder 52 is varied, so that the flow rate of the medicinal solution that enters the inside can be varied.

(Second Modification)

Figure 22:
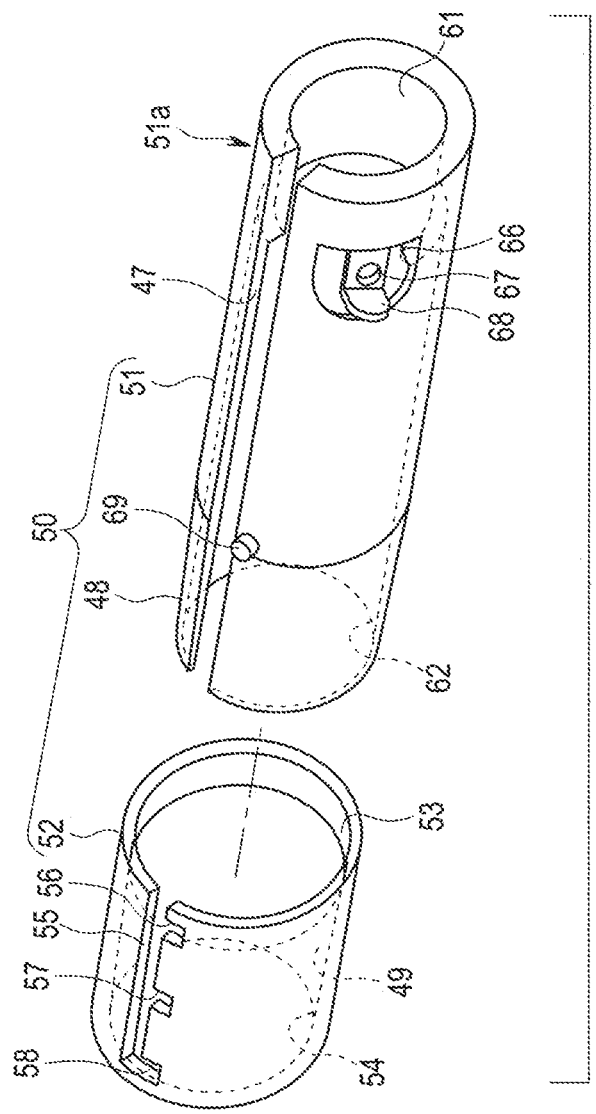
FIG. 22 is an exploded perspective view illustrating a configuration of the distal end attachment of a second modification.
Figure 23:
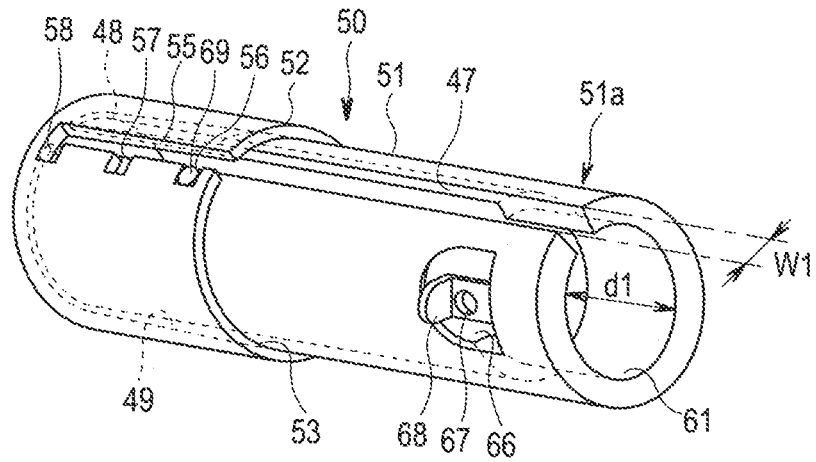
FIG. 23 is a perspective view illustrating a configuration of the distal end attachment in the first state in which the locking pin is locked into the first locking groove according to the second modification.
Figure 24:
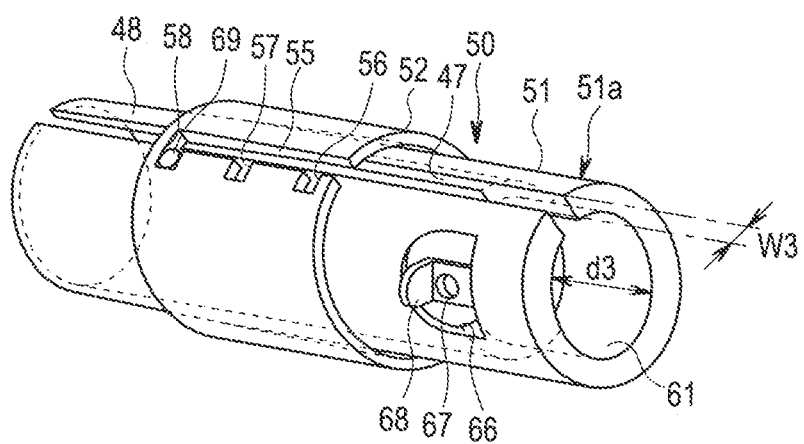
FIG. 24 is a perspective view illustrating a configuration of the distal end attachment in the third state in which the locking pin is locked into the third locking groove according to the second modification.
Figure 25:
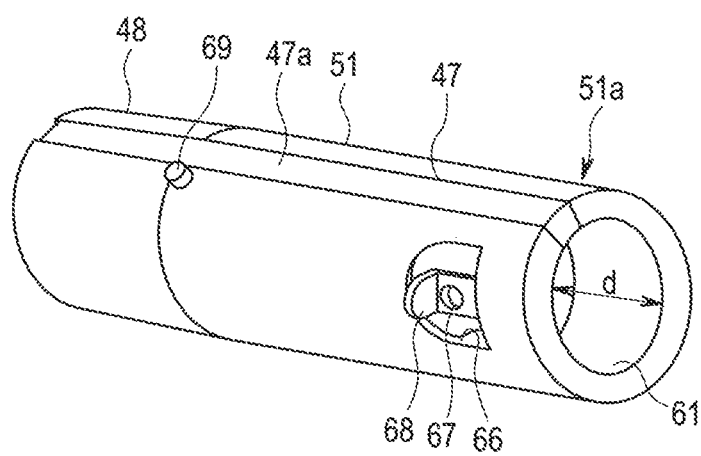
FIG. 25 is a perspective view illustrating a configuration in which an elastic member is disposed in a slit of a main body cylinder.

FIG. 22 is an exploded perspective view illustrating a configuration of the distal end attachment of a second modification, FIG. 23 is a perspective view illustrating a configuration of the distal end attachment in the first state in which the locking pin is locked into the first locking groove according to the second modification, FIG. 24 is a perspective view illustrating a configuration of the distal end attachment in the third state in which the locking pin is locked into the third locking groove according to the second modification, and FIG. 25 is a perspective view illustrating a configuration in which an elastic member is disposed in a slit of a main body cylinder.

As illustrated in FIG. 22, the distal end attachment 50 serving as the endoscope attachment of this modification is configured by the main body cylinder 51 in which, instead of the three opening windows 63, 64, and 65, a slit 47 at a predetermined width is formed in a longitudinal axis direction, and the slide cylinder 52.

In the main body cylinder 51, a tapered outer circumferential surface 48 having a diameter that is gradually decreased towards the proximal end side is formed on the outer circumferential surface of the proximal end part from the vicinity of the locking pin 69. In the slide cylinder 52, a tapered inner circumferential surface 49 having a diameter that is gradually decreased towards the proximal end side is formed on an inner circumferential surface.

The distal end attachment 50 herein has a configuration in which the slide cylinder 52 is attached to the main body cylinder 51, and in accordance with the position of the slide cylinder 52, the tapered inner circumferential surface 49 is in surface contact with the tapered outer circumferential surface 48 to vary a width of the slit 47.

More specifically, as illustrated in FIG. 23, in the distal end attachment 50, in a state in which the locking pin 69 of the main body cylinder 51 is locked into the pin locking portion 56 serving as the first locking groove of the slide groove 55 formed in the slide cylinder 52, the slit 47 of the main body cylinder 51 has a predetermined slit width W1.

At this time, the main body cylinder 51 is put into the first state in which the tapered inner circumferential surface 49 of the slide cylinder 52 is simply in contact with, or has a predetermined gap to, the tapered outer circumferential surface 48, and the opening portions 61 and 62 have a predetermined opening diameter (d1, only the opening portion 61 side is illustrated in the drawing) in an initial state.

As illustrated in FIG. 24, in the distal end attachment 50, in a state in which the locking pin 69 of the main body cylinder 51 is locked into the pin locking portion 58 serving as the third locking groove of the slide groove 55 formed in the slide cylinder 52, the diameter of the main body cylinder 51 is decreased, and the slit 47 has a slit width W3 (W1>W3) smaller than the slit width W1 in the first state.

At this time, the main body cylinder 51 is put into the third state in which the tapered inner circumferential surface 49 of the slide cylinder 52 is in surface contact with the tapered outer circumferential surface 48, and the diameters of the opening portions 61 and 62 are decreased from the initial state corresponding to the first state and varied to a predetermined opening diameter (d1>d3, only the opening portion 61 side is illustrated in the drawing) that is smaller than the opening diameter d1 in the first state.

Note that although not illustrated in the drawing, in the distal end attachment 50, in a state in which the locking pin 69 of the main body cylinder 51 is locked into the pin locking portion 57 serving as the second locking groove of the slide groove 55 formed in the slide cylinder 52, the diameter of the main body cylinder 51 is decreased, and the slit 47 is set to have a slit width that is smaller than the slit width W1 in the first state and larger than the slit width W3 in the third state.

At this time, the main body cylinder 51 is put into the second state in which the diameters of the opening portions 61 and 62 are decreased from the initial state corresponding to the first state but increased from the third state and varied to a predetermined opening diameter that is smaller than the opening diameter d1 in the first state and larger than the opening diameter d3 in the third state. In this manner, in the distal end attachment 50, the slit 47 is disposed in the main body cylinder 51, and the slit width and the opening diameter of the main body cylinder 51 can be varied in the three stages herein in accordance with the position of the slide cylinder 52.

Even with such a configuration, in the distal end attachment 50, the flow rate of the medicinal solution that enters from the slit 47 of the main body cylinder 51 and the opening portions 61 and 62 to the inside can be changed in accordance with the intensity and weakness of the cleaning disinfection property and the chemical attack property.

Note that as illustrated in FIG. 25, a configuration may also be adopted in which the slit 47 of the main body cylinder 51 is filled with an elastic member such as rubber, and the opening diameter d of the main body cylinder 51 varies. Furthermore, a configuration may also be adopted in which the tapered outer circumferential surface 48 is formed on each end side of the main body cylinder 51, the slide cylinder 52 is disposed in the front and the back, and the opening diameter of the main body cylinder 51 is decreased.

(Third Modification)

Figure 26:
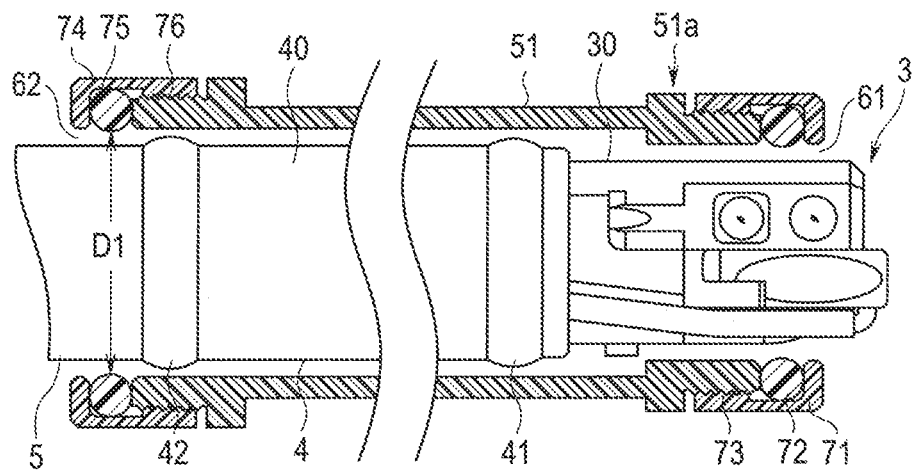
FIG. 26 is a partial cross-sectional view illustrating the distal end part of the insertion portion to which the distal end attachment in the first state is attached according to a third modification.
Figure 27:
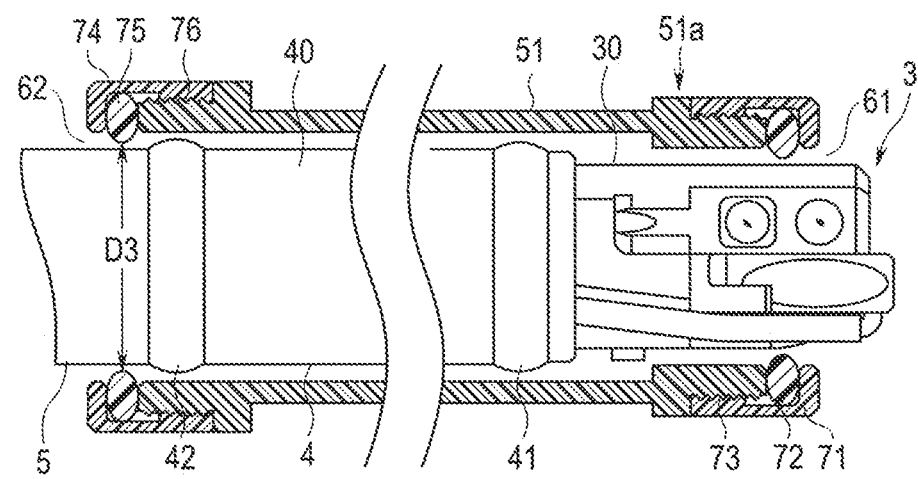
FIG. 27 is a partial cross-sectional view illustrating the distal end part of the insertion portion to which the distal end attachment in the third state is attached according to the third modification.

FIG. 26 is a partial cross-sectional view illustrating the distal end part of the insertion portion to which the distal end attachment in the first state is attached according to a third modification, and FIG. 27 is a partial cross-sectional view illustrating the distal end part of the insertion portion to which the distal end attachment in the third state is attached according to the third modification.

As illustrated in FIG. 26 and FIG. 27, the distal end attachment 50 of the present modification does not include the slide cylinder 52, but has pipe sleeves 71 and 74 having inward flanges screwed to screw portions 73 and 76 disposed at the distal end and the proximal end of the main body cylinder 51.

The distal end attachment 50 adopts a configuration in which O-shaped rings 72 and 75 are disposed between the inward flanges of the front and back pipe sleeves 71 and 74 and end surfaces in the front and the back of the main body cylinder 51, and the O-shaped rings 72 and 75 are tightened in accordance with screwing amounts of the pipe sleeves 71 and 74 to the main body cylinder 51 to vary opening diameters of the opening portions 61 and 62.

More specifically, as illustrated in FIG. 26, in a loose state in which the screwing amounts of the pipe sleeves 71 and 74 to the main body cylinder 51 are small, the O-shaped rings 72 and 75 are not collapsed, and the opening portions 61 and 62 have a predetermined opening diameter D1.

On the other hand, as illustrated in FIG. 27, in a tightened state in which the screwing amounts of the pipe sleeves 71 and 74 to the main body cylinder 51 are large, the O-shaped rings 72 and 75 are collapsed, the diameters of the opening portions 61 and 62 are varied to a predetermined opening diameter D3 that is smaller than the opening diameter D1 described above.

Note that herein, the distal end attachment 50 is put into the first state in which the opening areas are the largest when the opening portions 61 and 62 have the predetermined opening diameter D1, and the distal end attachment 50 is put into the third state in which the opening areas are the smallest when the opening portions 61 and 62 have the predetermined opening diameter D3.

In a state in which the screwing amounts of the pipe sleeves 71 and 74 to the main body cylinder 51 are tightened to approximately a half level from the first state, the opening areas of the opening portions 61 and 62 are put into the second state between the first state and the third state. Note that indices or the like may be disposed in the pipe sleeves 71 and 74 and the main body cylinder 51 to adjust the screwing amounts of the pipe sleeves 71 and 74 from the first state to the third state.

Furthermore, in accordance with the screwing amounts of the pipe sleeves 71 and 74 to the main body cylinder 51, the opening diameters of the opening portions 61 and 62 can also be continuously varied.

First Reference Example

Figure 28:
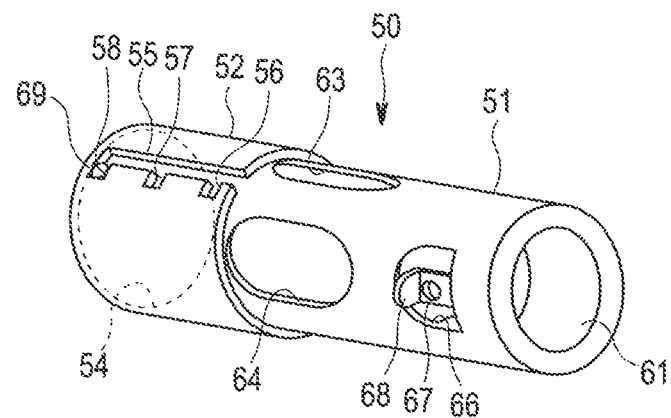
FIG. 28 is a perspective view illustrating a configuration of the distal end attachment in a short length state according to a first reference example.
Figure 29:
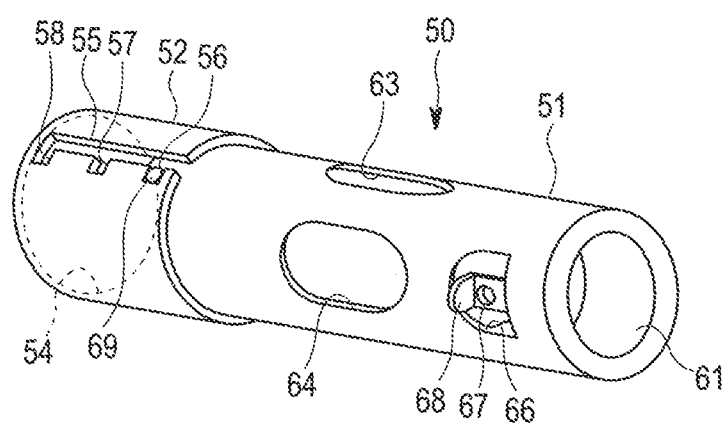
FIG. 29 is a perspective view illustrating a configuration of the distal end attachment in a long length state according to the first reference example.

FIG. 28 is a perspective view illustrating a configuration of the distal end attachment in a short length state according to a first reference example, and FIG. 29 is a perspective view illustrating a configuration of the distal end attachment in a long length state according to the first reference example.

As illustrated in FIG. 28 and FIG. 29, in the distal end attachment 50, when the locking pin 69 of the main body cylinder 51 is disposed on the proximal end side, the slide cylinder 52 can be varied between the short length state by being moved to the distal end side and the long length state by being moved to the proximal end side, and although the opening amounts (opening areas) of the three opening windows 63, 64, and 65 are not changed, by making it possible to adjust the coverage area on a hand side relative to a user including the thread wound bonding portion 42 on the proximal end side of the bending portion 4, the flow rate of the medicinal solution that enters from the opening portion 54 of the slide cylinder 52 to the thread wound bonding portion 42 may also be changed.

Second Reference Example

Figure 30:
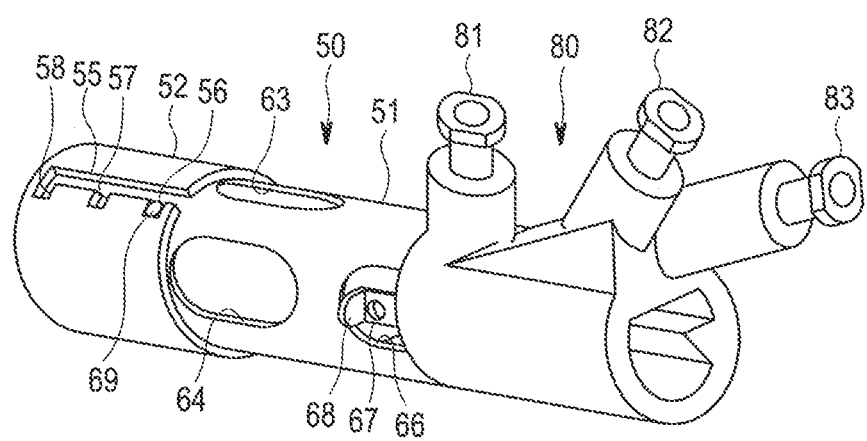
FIG. 30 is a perspective view illustrating a configuration of the distal end attachment in which a fluid supply portion is disposed according to a second reference example.

FIG. 30 is a perspective view illustrating a configuration of the distal end attachment in which a fluid supply portion is disposed according to a second reference example.

As illustrated in FIG. 30, the distal end attachment 50 may also adopt a configuration in which a fluid supply portion 80 is disposed in the distal end of the main body cylinder 51.

The fluid supply portion 80 has a plurality of, three herein, fluid supply connection ports 81, 82, and 83 such that flash cleaning of the circumference of the distal end rigid member 30 attached to the distal end attachment 50 can be performed in the medicinal solution such as the cleaning solution or the antiseptic solution. A fluid supply tube such as an endoscope cleaning machine or a syringe can be connected to the fluid supply connection ports 81, 82, and 83.

According to the present embodiment described above, the endoscope is illustrated by using the side-viewing endoscope as an example but is not limited to this, and endoscope auxiliary instrument can also be applied to a front-view type endoscope in which the raising base is disposed in the channel for allowing insertion of treatment instrument. Furthermore, it goes without saying that without the limitation to the endoscope, the endoscope auxiliary instrument can also be applied to the treatment instrument including the raising base in a distal end portion of an insertion portion such as a catheter.

Note that the present invention described above is not limited to only the embodiments described above, and various modifications can be implemented without departing from the gist of the invention.

What is claimed is:
1. An endoscope attachment comprising:
a first tube configured to cover a bonding portion formed of adhesive arranged in a bending portion of an insertion portion of an endoscope, the first tube having one or more openings; and
a second tube movably disposed on an exterior surface of the first tube, the second tube being movable relative to the first tube between a first position in which the one or more openings have a first liquid flow area exposed to an outside of the endoscope attachment and a second position in which the one or more openings have a second liquid flow area exposed to an outside of the endoscope attachment, the first liquid flow area being greater than the second liquid flow area, the second tube varying a flow rate of a liquid through the one or more openings;

wherein the one or more openings comprise a distal end opening of the first tube and a proximal end opening of the first tube;

the second tube comprises a distal end pipe sleeve and a proximal end pipe sleeve screwed to the distal end and the proximal end, respectively, of the first tube, the endoscope attachment further comprising a distal end O-ring that deforms radially in accordance with a screwing amount of the-distal end pipe sleeve and a proximal end O-ring that deforms radially in accordance with a screwing amount of the proximal end pipe sleeve; and the flow rate through the distal end opening and the proximal end opening varies based on the screwing amount of the distal end pipe sleeve and the screwing amount of the proximal end pipe sleeve, respectively.

2. An endoscope system comprising:

an endoscope comprising an insertion section, the insertion section having a bending portion with at least one bonding portion formed of adhesive; and an endoscope attachment detachably attachable to a distal end portion of the insertion portion, the endoscope attachment comprising:

a first tube configured to cover a bonding portion formed of adhesive arranged in a bending portion of an insertion portion of an endoscope, the first tube having one or more openings; and a second tube movably disposed on an exterior surface of the first tube, the second tube being movable relative to the first tube between a first position in which the one or more openings have a first liquid flow area exposed to an outside of the endoscope attachment and a second position in which the one or more openings have a second liquid flow area exposed to an outside of the endoscope attachment, the first liquid flow area being greater than the second liquid flow area, the second tube varying a flow rate of a liquid through the one or more openings.

3. The endoscope system according to claim 2, wherein:

the one or more openings comprise a plurality of first openings, the first tube is a first mesh tube having the plurality of first openings on an outer circumferential surface of the first mesh tube;

the second tube being a second mesh tube having a plurality of second openings on an outer circumferential surface of the second mesh tube; and the flow rate of the liquid through the plurality of first openings varies based on a rotational position of the first tube relative to the second tube.

4. The endoscope system according to claim 2, wherein:

the one or more openings comprise one or more opening windows on an outer circumferential surface of the first tube; and the second tube covers a first amount of the one or more window openings in the first position and covers a second amount of the one or more window openings in the second position, the second amount being greater than the first amount.

5. The endoscope system according to claim 2, wherein the at least one opening is arranged between the distal end side bonding part formed on the distal end side of the bending portion and the proximal end side bonding part formed on a proximal end side of the bending portion.

6. The endoscope system according to claim 2, wherein the second tube is configured to slide in a longitudinal axis direction of the first tube between the first position and the second position.

7. The endoscope system according to claim 2, wherein the one or more openings comprise a plurality of first openings, the first tube is a first mesh tube having the plurality of first openings on an outer circumferential surface of the first mesh tube;

the second tube being a second mesh tube having a plurality of second openings on an outer circumferential surface of the second mesh tube; and the flow rate of the liquid through the plurality of first openings varies based on a rotational position of the first tube relative to the second tube.

8. The endoscope system according to claim 2, wherein the one or more openings comprise a distal end opening of the first tube and a proximal end opening of the first tube.

9. The endoscope system according to claim 8, wherein the second tube comprises a distal end pipe sleeve and a proximal end pipe sleeve screwed to the distal end and the proximal end, respectively, of the first tube, and the endoscope attachment further comprising a distal end O-ring that deforms radially in accordance with a screwing amount of the distal end pipe sleeve and a proximal end O-ring that deforms radially in accordance with a screwing amount of the proximal end pipe sleeve; and the flow rate through the distal end opening and the proximal end opening varies based on the screwing amount of the distal end pipe sleeve and the screwing amount of the proximal end pipe sleeve, respectively.

10. The endoscope system according to claim 2, wherein the at least one opening is a slit extending longitudinally from a distal end to a proximal end of the first tube; and the second tube is configured to slide in a longitudinal axis direction of the first tube between the first position and the second position;

wherein the slit is wider in the first position than in the second position.

11. The endoscope system according to claim 10, wherein the first tube comprises an external taper and the second tube comprises a mating internal taper.

12. An endoscope attachment comprising:

a first tube configured to cover a bonding portion formed of adhesive arranged in a bending portion of an insertion portion of an endoscope, the first tube having one or more openings; and a second tube movably disposed on an exterior surface of the first tube, the second tube being movable relative to the first tube between a first position in which the one or more openings have a first liquid flow area exposed to an outside of the endoscope attachment and a second position in which the one or more openings have a second liquid flow area exposed to an outside of the endoscope attachment, the first liquid flow area being greater than the second liquid flow area, the second tube varying a flow rate of a liquid through the one or more openings;

wherein the at least one opening is a slit extending longitudinally from a distal end to a proximal end of the first tube;

the second tube is configured to slide in a longitudinal axis direction of the first tube between the first position and the second position; and the slit is wider in the first position than in the second position.

13. The endoscope attachment according to claim 12, wherein the first tube comprises an external taper and the second tube comprises a mating internal taper.

* * * * *